US006364834B1

(12) United States Patent
Reuss et al.

(10) Patent No.: US 6,364,834 B1
(45) Date of Patent: *Apr. 2, 2002

(54) METHOD AND SYSTEM FOR REMOTELY MONITORING MULTIPLE MEDICAL PARAMETERS IN AN INTEGRATED MEDICAL MONITORING SYSTEM

(75) Inventors: James L. Reuss, Waukesha; Renee S. Kirchner, Whitefish Bay, both of WI (US)

(73) Assignee: Criticare Systems, Inc., Waukesha, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/225,813

(22) Filed: Jan. 5, 1999

Related U.S. Application Data

(63) Continuation-in-part of application No. 08/747,859, filed on Nov. 13, 1996, now Pat. No. 5,855,550.

(51) Int. Cl.[7] .................................................. A61B 3/00
(52) U.S. Cl. ........................... 600/300; 705/3; 128/903; 128/904
(58) Field of Search ................................ 128/903–904, 128/900; 600/309, 481, 500, 529, 532, 538; 705/2–3

(56) References Cited

U.S. PATENT DOCUMENTS

| 3,646,606 | A | 2/1972 | Buxton et al. |
| 3,786,190 | A | 1/1974 | Pori |
| 4,494,553 | A | 1/1985 | Sciarra et al. |
| 4,517,982 | A | 5/1985 | Shiga et al. |
| 4,556,063 | A | 12/1985 | Thompson et al. |
| 4,883,057 | A | 11/1989 | Broderick |
| 4,958,645 | A | 9/1990 | Cadell et al. |
| 4,981,141 | A | 1/1991 | Segalowitz |
| 5,307,817 | A | 5/1994 | Guggenbuhl et al. |
| 5,349,953 | A | 9/1994 | McCarthy et al. |
| 5,381,798 | A | 1/1995 | Burrows |
| 5,410,471 | A | 4/1995 | Alyfuku et al. |
| 5,415,181 | A | 5/1995 | Hogrefe et al. |
| 5,416,695 | A | 5/1995 | Stutman et al. |
| 5,421,343 | A | 6/1995 | Feng |
| 5,452,356 | A | 9/1995 | Albert |
| 5,458,123 | A | 10/1995 | Unger |
| 5,462,051 | A | 10/1995 | Oka et al. |
| 5,481,255 | A | 1/1996 | Albert et al. |
| 5,534,851 | A | 7/1996 | Russek |
| 5,536,084 | A | 7/1996 | Curtis et al. |
| 5,553,609 | A | 9/1996 | Chen et al. |

(List continued on next page.)

FOREIGN PATENT DOCUMENTS

WO        WO 97/06499        2/1997

OTHER PUBLICATIONS

Technical Service Bulletin (Advertisement), Dawe's Laboratories, "Nutrition and Fedding Management of Baby Calves", No. 266, pp. 1–3. No date listed.

Primary Examiner—Robert L. Nasser
Assistant Examiner—Michael Astorino
(74) Attorney, Agent, or Firm—Reinhart Boerner Van Deuren, s.c.

(57) ABSTRACT

An integrated medical monitoring system comprising at least one patient monitor, at least one central monitor, and at least one remote access device which are tied together through an integrated communications link is disclosed. The communications between various components of the system are bi-directional, thereby affording the opportunity to establish monitoring parameters from remote locations, provide interactive alarms and monitoring capabilities, and provide data exchange between components of the system.

32 Claims, 7 Drawing Sheets

U.S. PATENT DOCUMENTS

| | | |
|---|---|---|
| 5,576,952 A | 11/1996 | Stutman et al. |
| 5,617,871 A | 4/1997 | Burrows |
| 5,619,991 A | 4/1997 | Sloane |
| 5,718,234 A * | 2/1998 | Warden et al. ............... 128/903 |
| 5,735,285 A | 4/1998 | Albert et al. |
| 5,754,111 A | 5/1998 | Garcia |
| 5,767,791 A * | 6/1998 | Stoop et al. ................. 128/903 |
| 5,944,659 A * | 8/1999 | Flach et al. ................. 128/903 |
| 5,959,529 A * | 9/1999 | Kail, IV ..................... 128/904 |

* cited by examiner

METHOD AND SYSTEM FOR REMOTELY MONITORING MULTIPLE MEDICAL PARAMETERS IN AN INTEGRATED MEDICAL MONITORING SYSTEM

This application is a CIP of Ser. No. 08/747,859 filed Nov. 13, 1996 now U.S. Pat. No. 5,855,550.

This invention relates generally to medical parameter monitoring and more particularly to an integrated medical monitoring system for use in a clinical setting. The medical monitoring system includes local patient monitors, remote central stations, and remote access devices, all of which are preferably networked together through a wireless communication system to provide overall patient care as well as data storage and retrieval through a single system. The communications between various components of the system are bi-directional, thereby affording the opportunity to establish monitoring parameters from remote locations, provide interactive alarms and monitoring capabilities, and provide data exchange between components of the system.

BACKGROUND OF THE INVENTION

Although systems for remote medical monitoring of patient physiological parameters are presently available, these systems suffer from some notable disadvantages. Some systems depend on a hardwired system which requires that patients be disconnected from a monitor, connected to a mobile monitor in transit, and then reconnected to the system at a new location. Furthermore, an additional monitor and often different sensor devices must be attached to the patient when the patient is in transit. These systems, therefore, are inefficient for use in clinical settings where patients are frequently transferred between various facilities.

Other systems employ wireless communications, but these are generally unidirectional RF transmissions from the monitor to the remote display only. Typically, physiological signal data is transmitted in analog form. The analog signal quality received at the remote display/control unit tends to be dependent upon the distance from the transmitter to the antenna(e); objects (building components, movable objects, etc.) in between the transmitter and receiver may compromise performance. Furthermore, transmission technologies such as UHF, which employ a particular base frequency for data transmission, face serious problems due to interference from other transmission sources which happen to be transmitting at or near the same frequency. These systems, therefore, suffer from low quality signals. Furthermore, due to the unidirectional nature of the communications, the care giver at the remote location cannot select which data is necessary to properly monitor a given patient, or select value ranges for various types of monitoring. Remote patient monitoring, therefore, is limited to performing preprogrammed tasks.

In still other cases, physiological data is initially filtered to determine when a limit has been reached, and an alarm is transmitted to a viewing station only when a predetermined alarm limit has been met. While generally providing a paging function, these devices do not provide for remote monitoring in a clinical setting or the transfer of large amounts of data.

Due to the limited communications between monitors and remote viewing locations, data transfer between systems is also problematic in prior art systems. Data collected in one remote display/control device must be loaded to a floppy disk or other transportable memory device and transported to another system. Therefore, it is difficult to maintain an electronic database of patient information for recordation, archiving, or analysis purposes.

Furthermore, when an emergency situation occurs, prior art systems generally require a relatively long time period to determine that an emergency has occurred and to broadcast the signal to a remote caregiver. This delay is extremely important in critical care monitoring, where a matter of seconds can make a significant difference in the outcome of a patient experiencing a life-threatening condition. For example, most available medical alert systems do not include an integrated paging system for providing appropriate information to a remote caregiver. Instead, an external paging system is often connected. These external paging systems must access a clinical database, search the data collected in databases for emergency situations, and determine when to provide a paging signal. These steps require that communication links be established between disparate equipment, and that a significant amount of data be processed before an emergency is detected, thereby wasting critical time. Furthermore, once an emergency situation is found, prior art systems generally provide a paging signal through a standard paging system. Publicly available paging and other communication systems, however cannot be controlled by the user. Frequently, these systems are overloaded at peak use times, thereby adding a further delay to the delivery of a medical alert system Other problems associated with prior art medical alert systems include difficulties associated with controlling the broadcast of a message and difficulties associated with determining whether an emergency message has been received. The public communications systems relied on many medical systems are prone to failure or to closure due to business decisions or bankruptcies. A medical alert system relying on such a communications system can, therefore, suddenly discover that it has lost medical alert capabilities. Furthermore, prior art systems often do not provide the communications systems necessary to alert the sending system that a message has been received, read, or responded to by a caregiver, or to determine whether a receiver is activated and capable of receiving a message.

Other prior art systems which incorporate wireless communications often depend on FM or other types of communication links which are prone to interference, have limited bandwidth capabilities, and generally provide insufficient data to a caregiver receiving a page. Furthermore, these devices often do not include a reply or response system which can guarantee that a message has been received, or that the receiving device is operational.

Prior art monitoring systems often also require the manual transfer of information to patient medical records, including waveform data which is often printed from a monitoring device, and is then cut and pasted into the patient's medical records. Manual record keeping of this type, including the manual entry of prescription data, physiological data, and even insurance and billing data, is prone to error.

There remains a need, therefore, for an integrated medical monitoring system which provides bi-directional, wide bandwidth communications between a number of elements including patient monitors, central monitoring systems, medical alert systems, and analysis systems to allow both monitoring and sharing of collected data for data intensive physiological parameters and waveforms. Such a system preferably would include an electronic data entry system such as a bar code scanner or other device to simplify entry of data, and to simplify transfer of data to an overall clinical information system. Preferably the clinical information system would include data such as billing and insurance information, laboratory results, and vital sign and waveform information in electronic medical records.

It is therefore an object of the invention to provide an integrated medical monitoring system which includes local patient monitors, central viewing stations, and remote access devices, and an electronic data entry system.

It is another object of the invention to provide an integrated medical monitoring system including patient monitors, central monitoring systems, and remote access devices using bi-directional data transmission.

It is a further object of the invention to provide a novel medical monitoring system that enables dynamic control of remote monitoring simultaneously with medical parameter and/or waveform data acquisition.

It is yet another object of the invention to provide an improved medical monitoring system which can receive and control a plurality of medical parameters and/or waveforms being monitored at remote locations.

It is a further object of the invention to provide a component which can be used therewith to automatically acquire and store data pertaining to various physiological parameters.

It is yet another object of the invention to provide a telemetry system which enables automatic acceptance of patient data and immediate analysis thereof and/or comparison with previously-acquired data.

It is another object of the present invention to use RF communication and automatic registration of critical data, as well as in combination with frequency hopping, spread spectrum technology, to provide significantly improved results which are surprising and unexpected in view of the prior art.

It is further object of the invention to provide a medical monitoring system which enables transmission of messages, including medical alert, from the central monitoring system to wireless, remote access devices, which may themselves reply or communicate with each other.

It is yet another object of the invention to provide a medical monitoring system in which medical alert messages can be automatically formatted to include time of alert, patient identification, patient location, alert condition and priority, vital signs data, and physiological waveform data.

It is a further object of the invention to provide a medical monitoring system in which secure delivery of a medical alert message can be guaranteed by utilizing an integral wireless communications system, and through monitoring for responses from the remote access device to the medical alert.

It is yet another object of the invention to provide a medical monitoring system which enables maintenance of the remote access device's message memory in such a way as to guarantee that space is available for new medical alerts.

It is yet another object of the invention to provide a medical monitoring system which enables automatic transfer of patient data from the central monitoring system to auxiliary systems for analysis, display, storage and/or retrieval.

SUMMARY OF THE INVENTION

The present invention comprises an integrated medical monitoring system preferably including at least one local patient monitor, at least one central monitoring system, and at least one remote access device. These components are linked in a network which preferably comprises a wireless RF system. Most preferably, the communications links comprise frequency-hopping, spread spectrum RF communications in the ISM frequency band. However, other wireless communication systems, including IR, may also be used.

The local patient monitor provides sensors for monitoring a number of physiological parameters including but not limited to ECG (electrocardiogram), NIBP (non-invasive blood pressure), $SpO_2$ via pulse oximetry, respiration, temperature, invasive pressure lines, gas monitoring, and cardiac output. The local patient monitor preferably includes a transceiver, or a transmitter and a receiver, a display and keyboard. The patient monitors can operate independently as a monitoring device, as well as transmit data to and receive monitoring control signals from a central monitoring system. To facilitate entry of data such as patient identity, caregiver identity, pharmaceuticals received, and various other data, the patient monitor preferably includes an electronic data entry device such as a bar code scanner, which can provide coded patient information to transmit to the central monitoring system or a clinical information system, as will be described below.

The central monitoring system comprises a display, a transceiver or a transmitter and a receiver, and memory storage for storing patient data. The central monitoring system receives data from the local patient monitors, displays this information to caregivers at the central monitor, and stores the data for archival and analysis purposes. Preferably, archival records associated with a given patient can be transferred to another central monitoring system or an auxiliary system either through wireless communications or through a hardwired network link between two or more central monitoring systems. A caregiver at the central monitoring system can select among the subset of available waveforms and vital sign data most appropriate for remote display, and this selection is transmitted to the patient monitor. The central monitoring system preferably also includes a scanner for facilitating data entry and retrieval of stored waveforms. The central monitoring system can store timed events, including timed activity charts which show a patient's physiological response versus various activity and exercise levels.

The central monitoring system also monitors incoming data from the patient monitor for medical alert messages, and continually monitors incoming data for possible emergency situations. When an emergency is found, the central monitoring system directly alerts the remote access device through the wireless transceiver. This integrated system eliminates processing and communication steps common in prior art devices. Preferably, the communication link is via a spread-spectrum RF system in the ISM band, thereby providing a high bandwidth transmission with limited extraneous interference, permitting the transfer of continuous waveforms and detailed vital sign information to a remote access device with limited interference.

The remote access device can comprise any of a number of electronic devices including paging systems; personal digital assistants (PDAs); telephones; or laptop, desktop, or other types of computers. Preferably, these devices are fitted with a transceivers to receive data from and transmit data to the wireless communications network described above. Due to the bandwidth of these communications, a significantly higher amount of data can be transmitted than in a standard paging system. Furthermore, because this system does not depend on communications through a standard pager system, problems associated with paging and cellular phone systems, such as busy or temporarily disabled or closed systems which might delay or prevent the receipt of a message, are averted. This is particularly important in applications in which an emergency or alarm signal is sent. Additionally, due to the bi-directional capabilities of the communications link, the sending system can determine that a caregiver has read and responded to a message. The sending system can also verify the availability of memory in a remote access device, and delete unnecessary messages to provide additional space. Therefore, the present invention provides a preferred system for medical alert system critical care monitoring, in that it is able to transmit the message in a timely fashion and verify that it has been delivered and read by an appropriate caregiver.

As noted above, the remote access devices preferably communicate bi-directionally. Due to these bi-directional communication capabilities, a caregiver can obtain updated information from the central monitoring system by requesting data from the remote access device. To facilitate such requests, remote access devices preferably include an electronic data entry device such as a bar code reader so that a caregiver in a remote location may easily scan a bar code to identify a given patient to obtain data. As noted above, the wide bandwidth of the wireless, preferably RF, system allows for a significant amount of data to be transmitted including vital sign statistics and waveforms of various physiological parameters. Because the devices can also communicate with each other, a first caregiver receiving such data in an alarm or other condition can also choose to forward the information to a second caregiver, or forward free-form text to the central monitoring system or the patient monitor itself. Such message may include care instructions or instructions to contact a specialist, thereby allowing a primary physician the opportunity to direct care remotely. Furthermore, although the remote device has been described as part of an overall system, it will be understood that such a device could be operated independently with one or more patient monitors including bi-directional communication capabilities as described above.

The remote access device can alternatively be operated as a medical alert system in which either the patient monitor directly contacts the remote device on discovering an alarm condition or the patient monitor transmits this information to the central monitoring system. The central monitoring system, in turn, transmits the information to the remote access device. The remote access device can include a GPS or other locating system which allows the sending system, whether the patient monitor or the central monitoring system, to determine the location of a plurality of caregivers and select an appropriate primary recipient of the alarm message based on location. The alarm system preferably determines an initial primary recipient based on location, specialty, and/or relationship to the patient (i.e. the patient's primary physician), and then waits for a signal from the remote device indicating that the message has been received and read. Preferably, this signal is sent automatically, although in some cases the recipient may send a coded response such as a password to the system. If a response is not received within a preselected time period, or if the response is negative, the message is sent to one or more secondary recipients. Preferably, the primary device receives a list of secondary recipients and the preselected time frame to forward the message and the primary device notifies the secondary device without further interaction with the sending system. Alternatively, however, this function can be handled by the sending system.

The central monitoring system further comprises a maintenance function which employs the bi-directional communication link between the central monitoring system to verify the available memory space and working status of the remote access devices. The central system can evaluate the data in the remote access device memory and delete unnecessary messages to assure that the device is operational for future data deliveries. Furthermore, upon delivery of data to a remote access device, the central monitoring system can detect when data has been secured and when data has been read. This function is particularly useful in time-sensitive medical emergency situations.

Preferably, the medical monitoring system also comprises at least one auxiliary system for transmitting and receiving clinical data, thereby providing a more complete overall medical monitoring and recordation system. The auxiliary system can be connected to the medical monitoring system via a hardwired network link, or through a wireless communication link. The auxiliary equipment can comprise a diagnostic workstation such as an ECG diagnostic workstation, a clinical information system, or other database system. Diagnostic workstations receive selected archived physiological data such as vital sign data, waveforms, timed cardiac events, or other events from the central monitoring system or a patient monitor for further clinical analysis by a caregiver. Clinical information systems store patient medical records such as demographics, assessments, diagnoses, care plans, notes, physiological waveform data, vital signs, laboratory, and other results, prescription and pharmacy information, insurance and billing information, and other personal patient information. Preferably, the information in the clinical information system is coordinated based on an identification number assigned to a patient when entering the hospital. This number, represented as a bar code, can the be used by the patient monitor and the central monitoring system to simplify the storage, retrieval, and transfer of patient data. Preferably, therefore, all devices through which data is entered, archived or retrieved include a bar code scanner or other electronic entry device.

Other objects, features and advantages of the present invention will be apparent from the following description of the preferred embodiments, taken in conjunction with the accompanying drawings described below wherein like components have like numerals throughout several views.

DETAILED DESCRIPTION OF THE PREFERRED EMBODIMENTS

Figure 1:
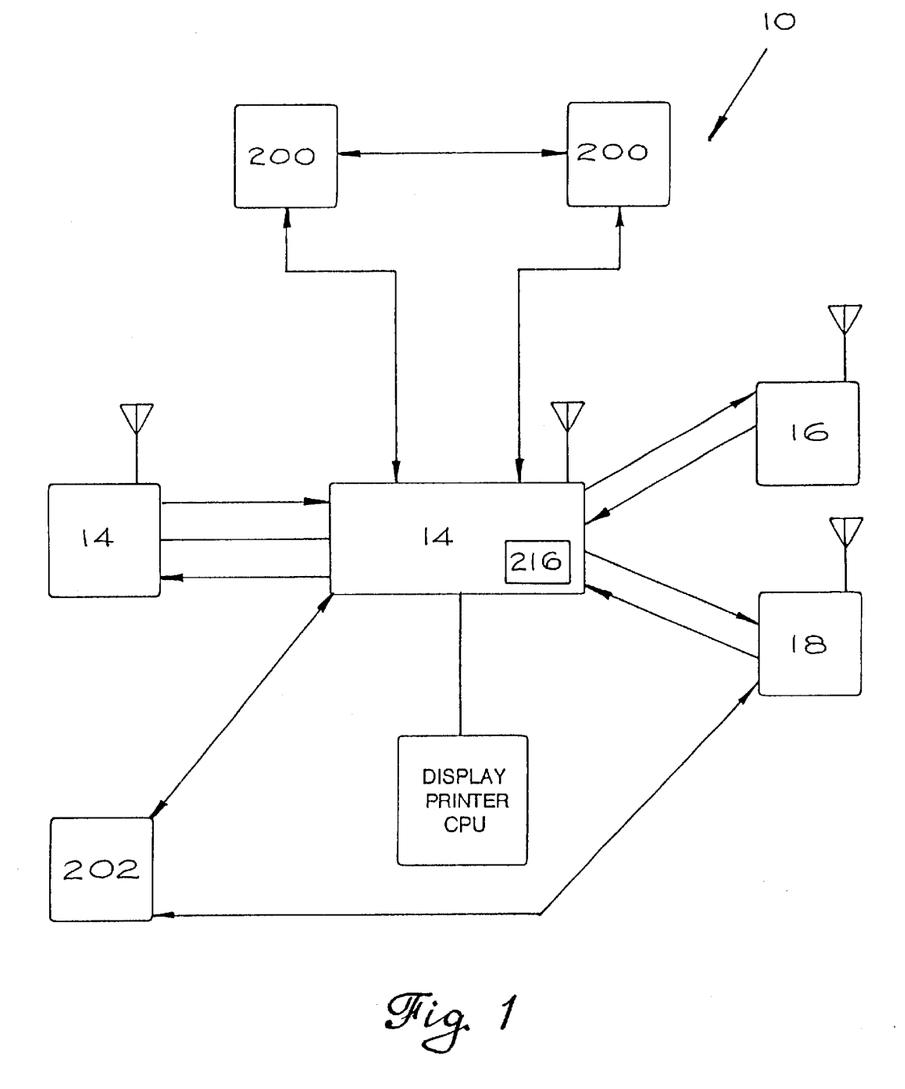
FIG. 1 is a block diagram of a medical monitoring system constructed in accordance with one form of the invention.

Referring to the figures and more particularly to FIG. 1, a medical monitoring system constructed in accordance with one form of the invention is shown generally at 10. The medical monitoring system 10 comprises at least one central monitoring system 14, at least one patient monitor 16, and one or more remote access device 200. Preferably, the monitoring system further comprises at least one auxiliary device 202 which may comprise a remote analysis device or a clinical information system, as will be described more fully below.

This preferred embodiment of the invention transmits remotely monitored digital medical data using bi-directional, preferably spread-spectrum RF transmission of digital data which can include forward error correction. Bi-directional transmission permits communications between all of the components of the system.

Through bi-directional communications, the central monitoring system 14 controls the remote monitoring process completely, including selection of medical parameters and/or waveforms to be determined by a patient monitor 16 borne by the patient or located at bedside. This ability to control the patient monitor 16 is important in supporting a broad range of different types of patient monitors 16, from small ambulatory monitoring devices to large bedside monitors with a broad assortment of monitoring capabilities. By permitting dynamic configuration, the mix of patient monitors 16 can change to suit the current patient population. A further feature of this preferred embodiment is the ability to identify the location of a patient being monitored by the system. Additionally, these bi-directional capabilities enable messages to be sent directly from the central monitoring system 14 or devices coupled thereto to the patient monitor 16 or devices coupled thereto. For example, a nurse can respond to a call signal initiated by the patient by sending a message from the central monitoring system 14 to an alphanumeric display at bedside. Methods for direct digital signal formation from input signals produced by a sensor device can be used with preferred embodiments of the invention, and U.S. patent application Ser. No. 08/683,617 is incorporated by reference herein in its entirety for further details regarding such digital signal formation techniques and its incorporation as part of a combination of elements.

The present invention also offers automatic patient registration through wireless communication once the patient monitors 16 are connected to the patient as described below. This facilitates an immediate acquisition of any and all parameters and/or waveforms associated with the central monitoring system which may be applicable to the respective patient. These parameters and/or waveforms can comprise ECG (electrocardiogram), NIBP (non-invasive blood pressure), SpO$_2$ via pulse oximetry, respiration, temperature, invasive pressure lines, gas monitoring, cardiac output, alarms, remote recording, and transmitter ID number, as well as other relevant patient information. Further, the bi-directional capabilities of the present invention allow selection of which parameters or waveforms to monitor with patient monitors 16 from the remote, central monitoring system 14. Additionally, the data sampling rates and all other monitoring parameters can be changed remotely using the central monitoring system 14.

As mentioned above and as shown in the figures, the present invention can include an automated data acquisition and/or storage component. Such a component, in its various embodiments, can without limitation be incorporated for use in conjunction with the clinical analysis of transmitted data. This component accommodates automatic patient admission and facilitates the immediate transfer/receipt of data to a central monitoring system. When a patient is connected to a patient monitor, clinical data is at once available and can be analyzed for various diagnostic purposes. This aspect of the invention can allow for the immediate clinical presentation and analysis of ECG, NIBP, SpO$_2$, as well as other pertinent information. This automated component is preferably located in the central monitoring system 14 although it can be located in or coupled to one or more of the patient monitors 16 or other devices.

By way of comparison, the prior art—affording a telemetry interface limited to one or two parameters—is somewhat restrictive in that a central monitoring system must wait for manual acceptance of data transmitted to a central station. For example, an end user of the prior art must manually instruct a central receiving location to learn a transmitted ECG pattern before such data is available for further comparison and analysis. The acceptance delay inherent to the prior art can cause valuable clinical data to be irretrievably lost. In other instances, with manual acquisition and storage of data, substantial delays may occur before the data is available for evaluation. However, with the present invention, once the patient monitor 16 is activated, data can be acquired, stored and evaluated upon transmission/reception. For example, ECG data can be automatically stored and evaluated for comparison to future output ECG data by a central monitoring system 16. Invasive pressure lines, alarms, remote recording and transmitter identification can, without limitation, also be incorporated. The station can also, as needed, incorporate disk drive technology, preferably a 1.44 MB floppy disk drive, which enables a clinician to store and/or retrieve patient data. Alternatively, more intensive data storage such as optical disks, tape storage units, zip drives or other storage devices can be included in the central monitoring systems 14.

Referring, in part, to the figures, the data acquisition/storage component of this invention can, alternatively, be described in relation to other invention components. Data describing various physiological parameters can be displayed on conventional computer display monitors interfaced with the central monitoring system 14 or other receiving device hardwired or otherwise communicating with the central monitoring system 14. The central monitoring system 14 preferably includes a printer, a computer monitor, a CPU such as a conventional personal computer and a means for communicating with patient monitors, which might be a hardwired interface such as RS-232 or an RF transmitter, an RF receiver, or a mix of both. While a variety of spectrums and telemetry techniques can be used satisfactorily, preferably clinical and control information is transmitted via RF communication using ISM band technology in conjunction with forward correcting, frequency hopping, spread spectrum technology, to the central monitoring system 14 or other component.

Figure 4:
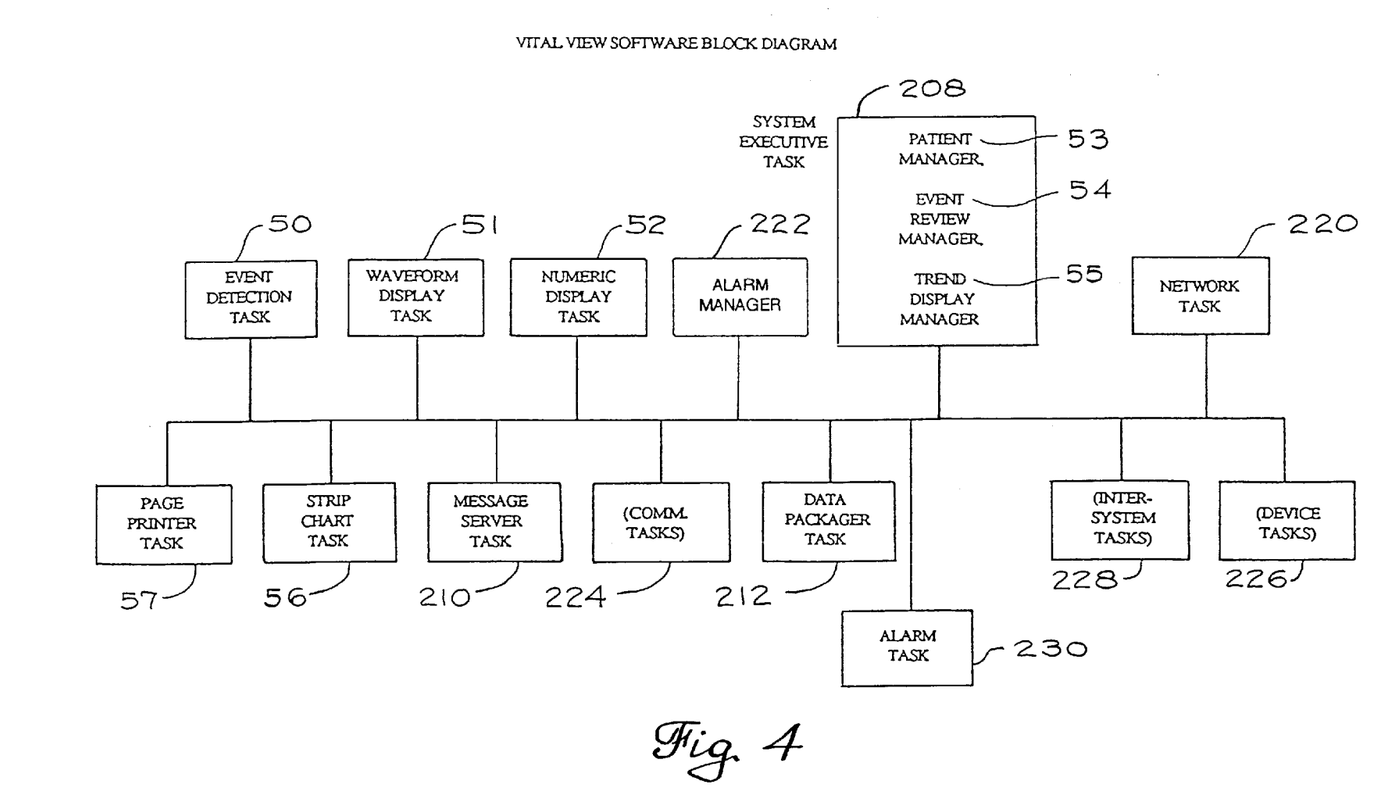
FIG. 4 is a block diagram illustrating software configurations and/or networks of one type which can be used in accordance with the central monitoring system of this invention.

Referring to FIG. 4, the central monitoring system 14 software incorporates a plurality of tasks operating under a real-time operating system. The incoming patient data is collected by the Data Packager Task 212, which interprets the communications protocol. One or more Communications Tasks 224 manage the communications hardware in use (e.g., hardwired serial interface, network interface). The patient data is then reviewed for anomalous situations, including alarm limit violations, by the Event Detection Task 50. Audible and visual alarms are created by the Alarm Task 230. The display of waveforms and numeric vital signs are handled by the Waveform Display Task 51 and the Numeric Display Task 52, respectively. The process of automatically or manually admitting a patient to the central station 14, and maintaining demographic information, is controlled by the Patient Manager 53.

In one preferred embodiment, patient information is entered and stored based on an overall patient bar code system. In this embodiment, an electronic entry system 206, preferably a bar code scanner, is coupled to the central monitoring system 14, and patient admission data is controlled by the Patient Manager 53 based on the coded identification number assigned to a given patient and represented on their person as a bar code. The coded identification number is then employed to maintain a database of patient information, including information collected by the central monitoring system 14 as described below. In this way, patient admission data, electronic test results including waveforms vital sign data, and events can be stored electronically in a single database.

The recording of alarm events, whether detected in the patient monitor 16 or the central monitoring system 14, takes place in the central monitoring system 14 through the Event Review Manager 54. Preferably, the event is a 36-second stored waveform chosen to bracket the time of the event. In this case, the central receiving central monitoring system preferably provides a display six seconds before the event, six seconds during the event, and for 24 seconds following the event. Other display sequences are possible. In preferred embodiments of this sort, the central monitoring system can analyze and store up to 100 events. Such events can be cataloged in an appropriate manner for easy retrieval, such as through an encoded bar code system as described above. Cataloged events can be used to provide a running total of events which can be reviewed and, as needed, compared to those events not yet reviewed. Events can also be reprinted, stored on a floppy disk, or deleted at any time according to standard operating procedure.

When the Event Review Manager 54 detects an alarm condition requiring immediate attention, or receives a signal from a patient monitor indicating such an event has occurred, a signal is forwarded to the Alert Server Task as will be described more fully below.

Comprehensive trending of such parameters as heart rate, blood pressure, $SpO_2$, respiration rate, etc. over time is available through the Trend Display Manager 55. A 24-hour trending capability is preferred. The trending can involve single or multiple parameters and is especially useful for cardiorespiratory patients, or those with other cardiovascular abnormalities. The Patient, Event, and Trend Managers together comprise the System Executive Task 208.

The printing of waveform and/or textual data is handled by the Strip Chart Task 56, if the printing is taking place on the AR-42 chart recorder, or by the Page Printer Task 57, if taking place on the page printer. Activity information is also tracked through time. This is especially valuable in monitoring during rehabilitation therapy, where clinical data is collected during exercise activities. This activity information can be displayed and printed in the trend alongside clinical data.

When a medical alert situation has been detected, a Message Server Task 210 processes requests for delivery of a message to a remote access device made by the System Executive Task 208. The Message Server Task 210 maintains a list of information on messages which have been queued, including status (sent, acknowledged, canceled, etc.). In addition to initiating delivery of a message, this task also determines if a delivery has failed, and optimizes use of the memory reserved for message storage inside of the remote access device. If a alert delivery fails, either because it could not be sent or was not acknowledged in a predetermined time period, the Message Server Task 210 can send an alarm to the central monitoring system or alternatively transmit the message to an alternative recipient. Any message to be sent to a remote access device, e.g., a medical alert message, is passed along to the appropriate Device Task (see below).

Because the Message Server Task 210 monitors a list of all messages sent in the system, it also performs the task of message memory maintenance for the remote access devices. Periodically, the Message Server Task 210 queries all known remote access devices 200 to determine if the message memory in some remote access device 200 is becoming full. If so, the Message Server Task 210 issues a command to the remote access device 200 to remove message(s) from its memory. The selection of messages is based upon age of the message, whether it has been read, and the priority of a medical alert (if any) associated with it. Furthermore, the Message Server Task 210 can delete data from the remote access device 200 which is no longer relevant, e.g., alerts which were responded to by other recipients and thus no longer need attention. A final advantage of this maintenance activity is that the central monitoring system 14 will know if a particular remote access device 200 is no longer available (e.g., battery low, has gone out of range, malfunctioning, etc.) by a lack of response to the maintenance query.

One or more Device Tasks 226 may be active in the system. Each type handles the details of communications with a particular type of remote access device (e.g., a pager versus a telephone or handheld computer). The Device Task 226 handles a request from a remote access device for information by accessing the patient, event, trend, and waveform data managed by the other tasks in order to format messages to be returned to the remote access device. In a preferred embodiment the Device Tasks 226 may utilize the same wireless communications infrastructure as the Data Packager Task 212. This reduces overall systems cost, and permits tighter control of delivery time for medical alerts. This does not preclude the use of a variety of remote access devices 200. E.g., with IP (Internet Protocol) telephony, it is possible for a Device Task 226 to generate data in synthesized speech to telephonic remote access devices utilizing the same wireless infrastructure as a conventional pager.

The Network Task 220 comprises the means by which multiple central monitoring systems coordinate with each other over a network. The Inter-System Tasks 228, if active, support communications with various auxiliary systems, such as ECG diagnostic workstations or clinical information systems.

Figure 2:
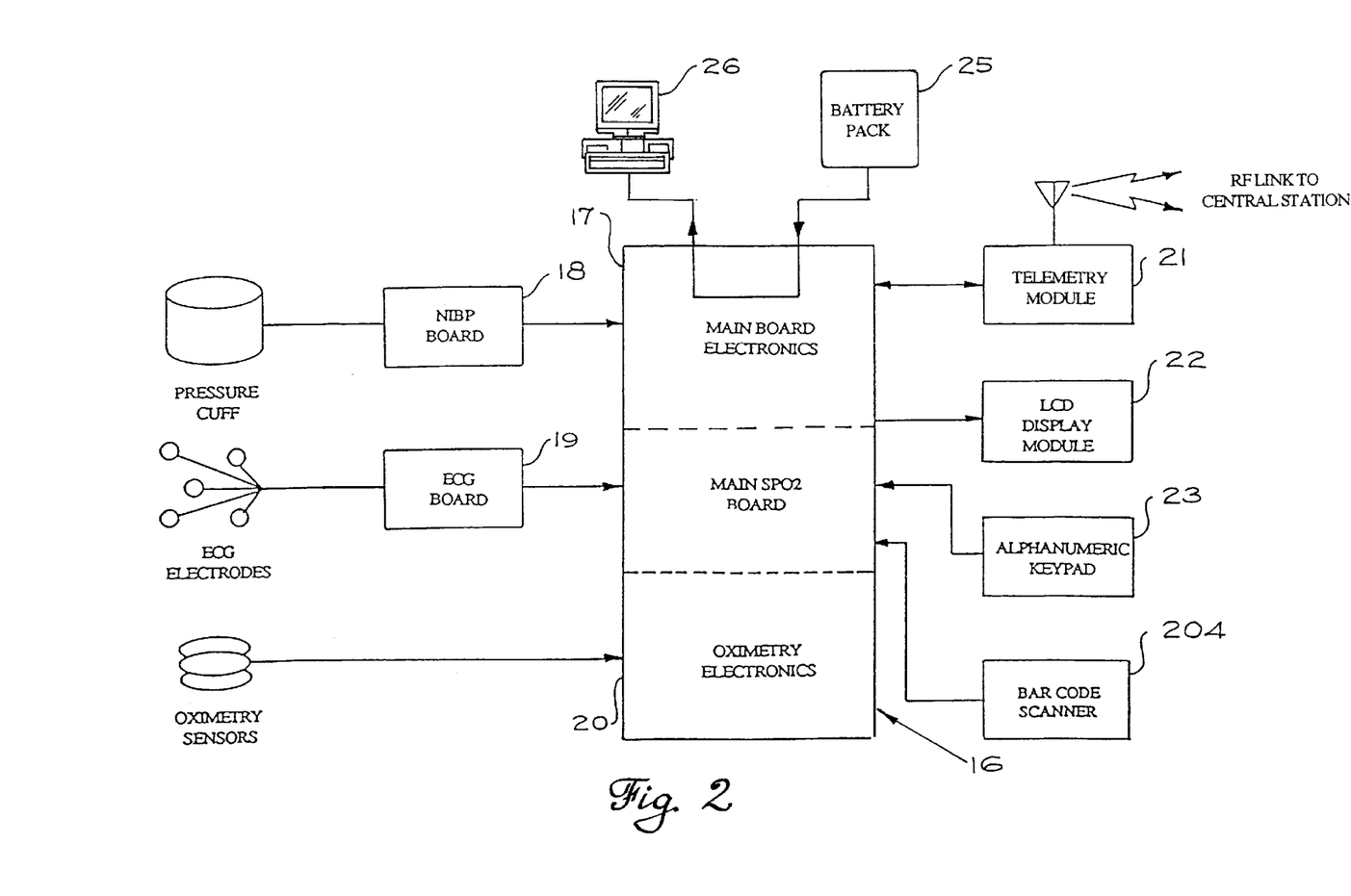
FIG. 2 is a block diagram showing one preferred embodiment of a patient monitor of the present invention.

A preferred embodiment of the patient monitor 16 is as presented through the multiple parameter telemetry patient monitor available under the MPT trademark from Criticare Systems, Inc. of Waukesha, Wis. Referring to FIG. 2, this preferred embodiment of the patient monitor 16 includes a main circuit board 17, NIBP monitor 18, ECG 19, and pulse oximetry 20; a telemetry module 21; a user interface composed of an LCD display module 22, keypad 23, and audio tone generation 24; and a battery pack 25. For factory and service support, a communications link, preferably RS-232, is provided for communicating with an external PC 26. Preferably an electronic entry device 204, such as a bar code scanner, is included on the patient monitor 16. The electronic entry device allows a user to scan data such as patient identification, drug therapy information, lab testing information, and activity testing information directly into the monitor, thereby preventing potential errors caused by manual data. Furthermore, this information can be transmitted to a central monitoring system and can be accessed by caregivers who require information about a specific patient by scanning the bar code on a chart or other documentation.

The NIBP 18 component of this embodiment utilizes oscillometric measurement upon inflation. It can average less than 40 seconds, standard adult cuff. Various automatic measurement cycles are available. Continuous readings are available for up to five minutes. Operative pressures range from 30–300 mm Hg for adults and 20–150 mm Hg for neonates. Such a component typically has an accuracy of +/–2% or +/–2 mm Hg over the full range of pressures. The pulse oximetry component 20 has a range of 0–99% $SPO_2$ level, with a resolution of 1%. Typically, accuracy is +/–2% (70–99%) and +/–3% (50–69%). Dual wavelength LED is a preferred method of operation.

The ECG 19 component utilizes band widths of 0.05–100 Hz and 0.5–40 Hz, and utilizes 3 or 5 electrodes to monitor two lead views simultaneously. Heart (pulse) rate is measurable over a range of 20–300 beats per minutes, with updates available from beat to beat. Such a component is accurate to +/–1 BPM or 1% (the larger) if derived from ECG, and +/–2 BPM or 2% (the larger) if derived from $SpO_2$ and NIBP. The central monitoring system 14 remotely select between the ECG leads to obtain a useable or optimal signal, based upon the status reported by the monitor and its own signal quality criteria (e.g., the amount of noise in the signal).

Referring to FIG. 2, it is shown that the patient monitor 16 also includes an LCD display module 22, keypad 23, and audio tone generator 24. The user interface permits the caregiver to locally select patient monitoring conditions, including what vital signs are to be monitored and how; adjust local display features including waveform selection, scaling, and sweep speed; and manually communicate back to the central station 14 to initiate functions such as remote printing or alert personnel associated therewith. In the event that patient moves outside of the wireless communications range of any central station 14, this user interface permits the caregiver to operate the monitor locally like a conventional bedside monitor.

Figure 5:
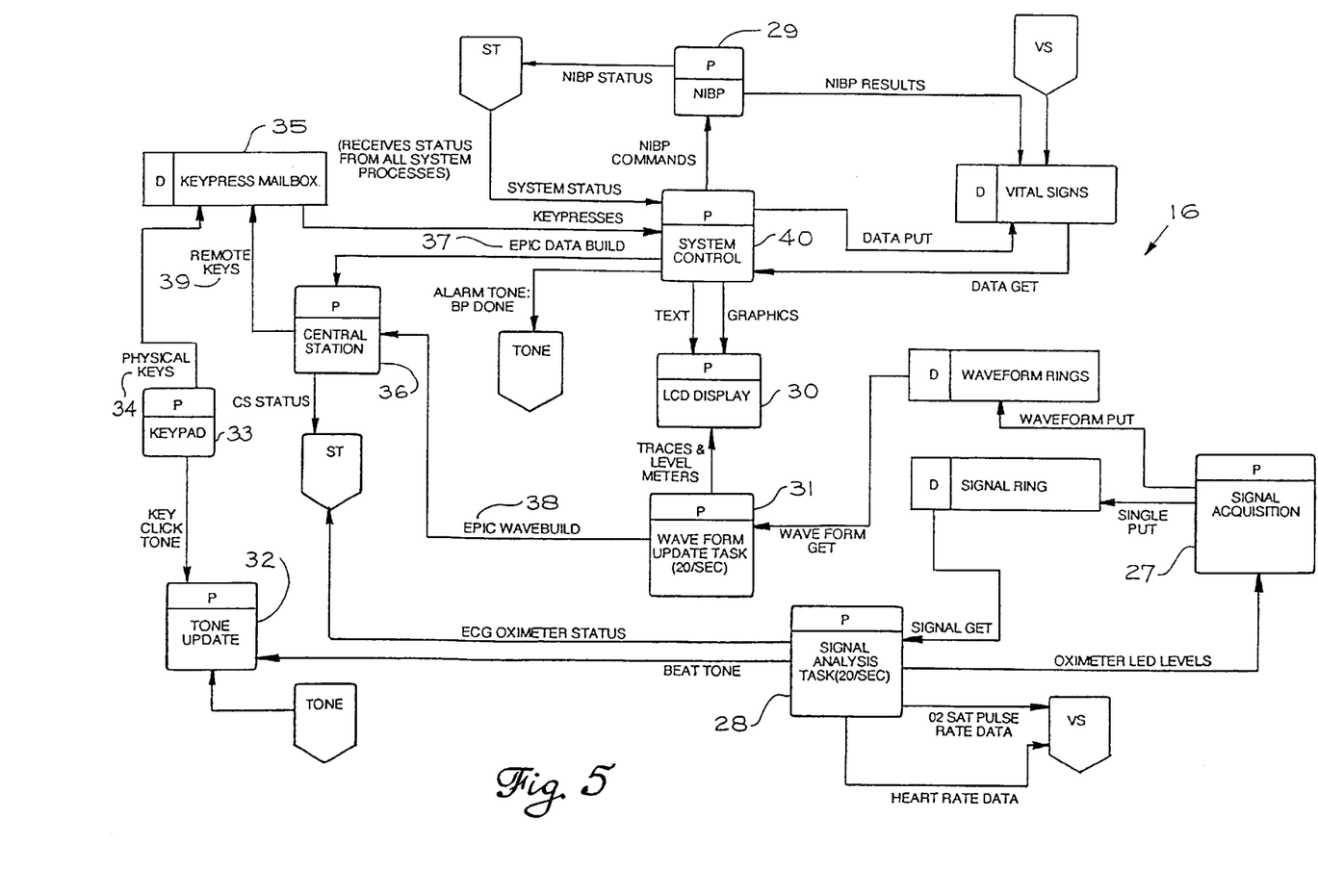
FIG. 5 is a block diagram showing a patient monitor constructed in accordance with one form of the invention.

The inclusion of both local and remote operation of a patient-borne monitor with bi-directional wireless communications makes the patient monitor 16 uniquely different from either conventional telemetry transmitters or bedside monitors retrofitted with transmitters. This poses a significant problem in local versus remote interaction, however, which is resolved in the software component of the monitor. Referring to FIG. 5, the software architecture of the patient monitor 16 is illustrated.

A System Control process 40 contains a body of software for coordinating processes in the monitor, providing common services, and managing shared resources. In the preferred embodiment, this includes a real-time operating system kernel, although other means of coordination such as "ladder logic" are available. The Signal Acquisition process 27, Signal Analysis Task 28, and NIBP process 29 are responsible for the conversion of analog signals from sensors in proximity to the patient's body into digital representation; processing of those signals including filtering and transformation; and interpretation of the processed signals to yield vital signs information. The local display is managed by the LCD Display process 30, receiving waveform data from the waveform Update Task 31 and textual data including numeric values from the System Control process 40. Audio tone generation is accomplished by the Tone Update process 32.

The local keypad input is handled by the Keypad process 33, which produces a series of messages labeled physical keys 34 sent to a Keypress mailbox 35. These messages are merely an ASCII representation of the key pressed; typically, one keypress is translated into one message to the mailbox, although the message representation allows a string of multiple keypresses. Other representations of the key pressed are possible, such as binary codes, bit masks, or software function addresses; these should all be considered within the spirit and scope of this invention. The Keypress mailbox 35 is periodically examined by the System Control process 40; any messages present are read, and the appropriate actions taken, including side-effects such as changing the content of menu items currently visible on the LCD display 22.

The Central Station process 36 is responsible for messages going to and from the central station 14 via the wireless communications. This includes transmission of EPIC data packets 37 (heart rate, blood pressure, etc.) as well as EPIC wave packets 38 (ECG and plethysmograph waveforms). As part of its logic, the Central Station process 36 interprets commands received from the central monitoring system 14, and creates a series of messages to the Keypress mailbox 35 labeled remote keys 39 to execute the indicated commands. Such messages contain additional coding indicating the source of the keypresses was the central monitoring system 14.

A mailbox such as the Keypad mailbox 35 operates as a FIFO (first-in, first-out buffer); i.e., the mailbox maintains the temporal order of messages sent and removed from it. By translating a series of one or more commands received from the central station 14 into a single remote keys message 39, the Central Station process 36 can ensure that a sequence of operations requested remotely is completed without interruption by local interactions represented by physical keys messages 34. Furthermore, any desired side-effects such as updating menu items visible upon the LCD display 22 will automatically take place. The System Control process 40, having available the fact that a keypress message originated remotely, can take further steps to reduce confusion of the local operator, including issuance of a warning tone 41, or inhibiting further local keypress processing for a period of time. The operations representing physical keys 34 and remote keys 39 are overlapping but not identical sets. Thus is it possible to prevent some local operations (e.g., zeroing an invasive pressure line) from being done remotely, and prevent some remote operations (e.g., switching a wireless communications channel selection) from being done locally. It should be apparent that other paradigms for representing a sequence of operations, such as a linked list of function calls, may also be useful for coordinating the local and remote operation, and fall within the spirit and scope of this invention.

Figure 3:
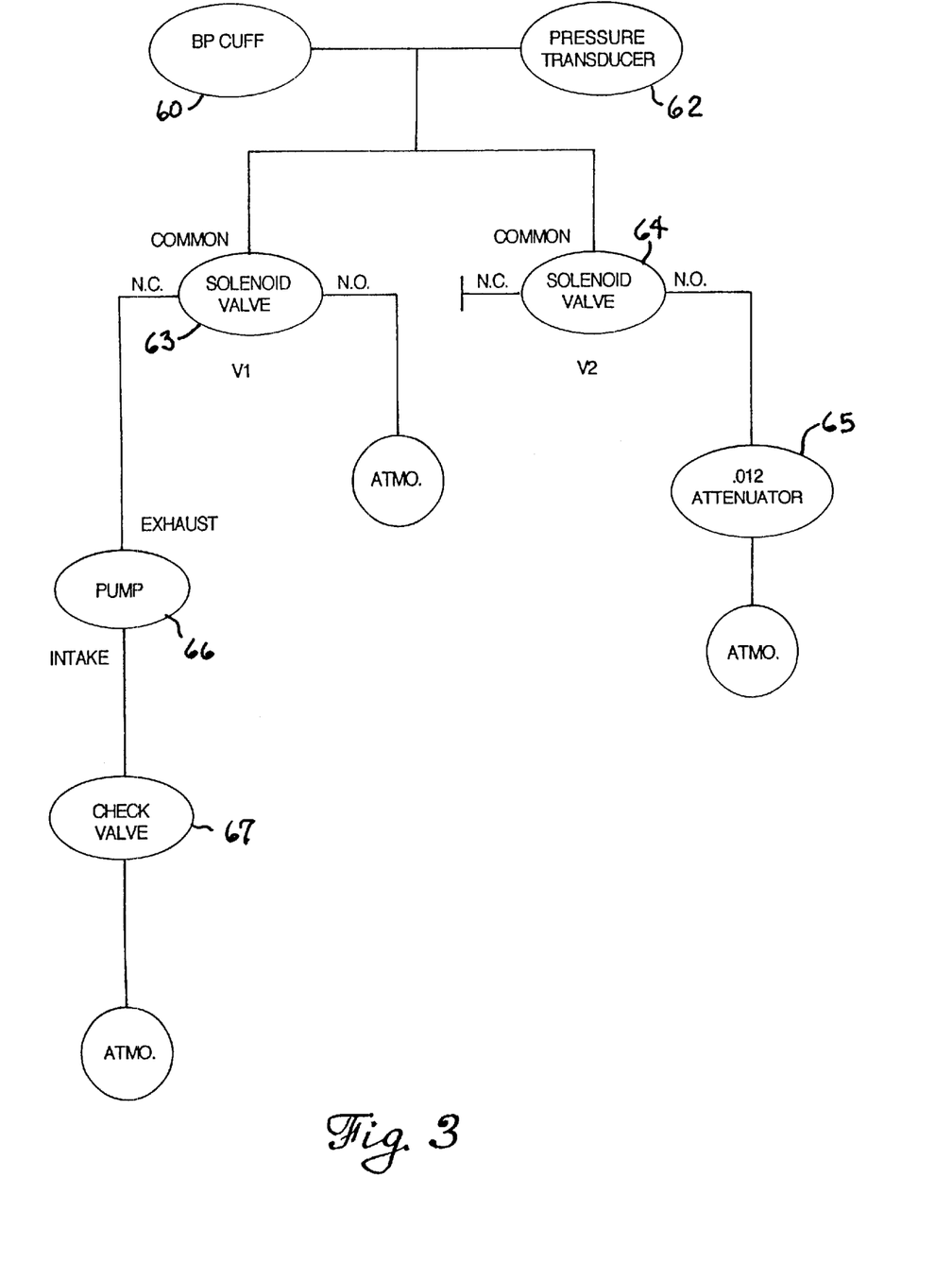
FIG. 3 is a schematic representation of the pneumatic function of a non-invasive blood pressure component of the type which can be used with a preferred embodiment of the invention.

The NIBP 18 included in the patient monitor 16 is designed specifically to reduce weight and power consumption for battery operation in ambulatory applications. Monitoring of NIBP in ambulatory patients has been uncommon due to the difficulty of creating a reliable, accurate NIBP device small enough to wear yet capable of inflating a broad range of BP cuffs. Most of the previous attempts have utilized deflation monitoring, i.e., rapidly inflating a cuff to well above the patient's blood pressure range, then releasing pressure while performing data acquisition. In the patient monitor 16, the NIBP monitoring is done during inflation, permitting the use of a smaller pump consuming lower peak power. Referring to FIG. 3, the NIBP board 18 is revealed to incorporate a unique pneumatic system facilitating inflation-mode monitoring using oscillometric technology.

A BP cuff 60, wrapped around a limb of the patient, is connected through a pneumatic system 61 to the remaining components, found within the patient monitor in conjunction with the NIBP board 18. The pressure transducer 62 accurately converts the pressure within the BP cuff 60 to an electrical signal, which may be processed and digitized on the NIBP board 18 prior to digital processing by the main board 17. The primary solenoid valve 63, commonly known as a "dump valve," provides for rapid deflation of the cuff after a reading is completed. The secondary solenoid valve 64, also known as the "bleeder valve", has an attenuator 65 on its port, chosen to yield a reduced flow rate into the BP cuff 60. In the absence of power, both solenoid valves are normally open to atmosphere. Lastly, a passive check valve 67 is included to prevent back-flow out of the pump 66 when it is not running yet pressure is to be maintained in the BP cuff 60.

Pressure in the BP cuff 60 can be dynamically controlled by the processor of the main board 17 controlling the pump 66 drive voltage on the NIBP Board 18. During normal readings on an adult, both the primary solenoid valve 63 and the secondary solenoid valve 64 will be closed, forcing all air flow from the pump 66 through the pneumatic system 61 and into the BP cuff 60. By implementation of a closed-loop control algorithm, it is possible to stabilize the rate of pressurization as desired to facilitate inflation-mode monitoring. For example, a PID (proportional/integral/differential) algorithm may includes use of the pressure transducer 62 signal (proportional), its integral, and/or its derivative. However, pumps of the type preferred in this invention for their smaller size, weight and cost cannot be driven effectively at lower voltages to achieve the low flows which may be needed for smaller cuffs, such as commonly used for infant and pediatric monitoring. In this event, the NIBP control algorithm can select to open the secondary valve 64, allowing some of the air flow to exhaust through the attenuator 65, and permitting the pump 66 to be run in a more ideal voltage range. Although a orifice internal diameter of 0.012" has been chosen in this case, other pump and orifice combinations fall within the spirit and scope of this invention.

Other parameters and waveforms that can be monitored include invasive pressures at multiple sites, respiration, body temperature, inspired and expired $CO_2$ levels in inspired and expired air, $O_2$ levels in inspired and expired air, anesthetic levels including nitrous oxide levels in inspired and expired air. It will be apparent to one of ordinary skill in the art that the patient monitors 16 can include any number of conventional monitoring devices for monitoring these parameters and waveforms.

With respect to particular RF specifications, the receiver frequency and transmitter frequency can be ISM 902–928 MHz although any legally permissible frequency range can be used. An internal antenna is preferably used with the frequency hopping spectrum spreading techniques which are well known in the art.

In accordance with another preferred embodiment of the invention, an external RF modem can be used with conventional bedside monitors such as those commercially available from the assignee of the present invention. The external RF modem can be used to communicate with the central monitoring system 14 instead of requiring a specially configured patient monitor 16 including RF transceivers or transmitter and receivers technology.

As indicated above, the present invention allows transmission of several physiological parameters simultaneously, through hardwire, wireless or other communication in contrast to the prior art, where simultaneous transmission is limited. The present invention overcomes such a limitation, without degradation of signal and without a slowdown in system function, by supporting the display of (possibly different) physiological signals at the patient monitor and the central station; by providing for transmission of multiple physiological signals from the patient monitor to the central station; and by providing the means to select which physiological signals will be collected at the patient monitor and/or transmitted to the central station. The advantages of independent local and remote control of the physiological data to be displayed has been discussed above.

Simultaneous transmission, alone or in conjunction with other components of the present invention, permits maintenance monitoring capabilities during the transport of the patient. For instance, a clinician using the present invention is able to transport the patient in such a way as to continuously monitor both invasive and non-invasive physiological parameters. By way of comparison, an end user of the prior art would necessarily disconnect the patient from a host monitor and reconnect that patient to a second monitor, one especially built for transporting the patient. The advance represented by the present invention assists the administration of health care. Continued, uninterrupted monitoring of all parameters and/or waveforms, both invasive and non-invasive, is possible throughout the transport and completion of a subsequent procedure. Furthermore, if hemodynamic monitoring circuits are involved, dispensing with the need to disconnect a patient will decrease the inclement risk of contamination. The patient can be transported immediately and when required, without delay due to changes in monitoring requirements. The continued, uninterrupted monitoring of all parameters and waveforms can be accomplished in several ways.

The bi-directional communication capability of the patient monitors 16 of the invention make it possible for the central station 14 to select, per patient and at any time, the subset of available waveforms and vital signs data most appropriate for remote display. In a more limited patient monitor, it may be possible to transmit two or three waveforms simultaneously at all times without exceeding the available communications bandwidth. However, a fully-featured bedside monitor may easily be collecting more waveforms than practical for transmission to and display at the central station 14. Available bedside monitors lacking bi-directional wireless communications offered no choice of the waveforms viewed remotely, or required direct caregiver interaction with the bedside monitor to select the remotely viewed waveforms. In the preferred embodiment, the bedside monitoring incorporates bi-directional wireless communication and software coordinating local and remote user interfaces, as disclosed herein.

In accordance with one preferred embodiment of the invention, a plurality of the central monitoring systems 14 are located throughout a facility and can communicate with one another via hardwire, wireless or other communication methods. Transfer of a patient from one central monitoring system 14 to another can be accomplished either by manually initiating a transfer function at the initiating central monitoring system 14, or can be accomplished automatically by sensing when a patient enters a zone allocated to another central monitoring system 14. The manual transfer method has the advantage of requiring personnel to consciously execute the command and monitor the results of the transfer. In this way, no patient is inadvertently lost by the system. Appropriate confirmation can be provided to ensure the transfer has been effectively completed. In accordance with the automatic transfer method, the fields of the central monitoring system 14 preferably overlap so that continuous monitoring from a central location can take place.

Alternatively, monitoring can be switched from central monitoring by the central monitoring system 14 to the patient monitors 16 in transit. When a transfer is completed, the patient can be automatically registered into the appropriate central monitoring system 14 to which the patient is being transferred. Communication between the central monitoring system 14 enable historical patient data to be transferred during or subsequent to the transfer procedure.

While a variety of techniques can be used, preferably the frequency band is divided into a number of discrete sub-bands. In frequency-hopping spread spectrum communications, the transmitters "hop" along a programmed sequence of frequency sub-bands in such a way as to avoid interference with each other. The hop sequences may be thought of as defining a set of non-interfering channels through time. Each of the central monitoring systems 14 can then operate on its own channel.

In accordance with another preferred embodiment of the invention, the central monitoring systems 14 can be accessed from another remote location, such as a lounge and interrogation of certain patient parameters and waveforms can be initiated. In this way, nurses or other personnel can monitor a patient while performing activities in locations other than a central monitoring system.

Figure 6:
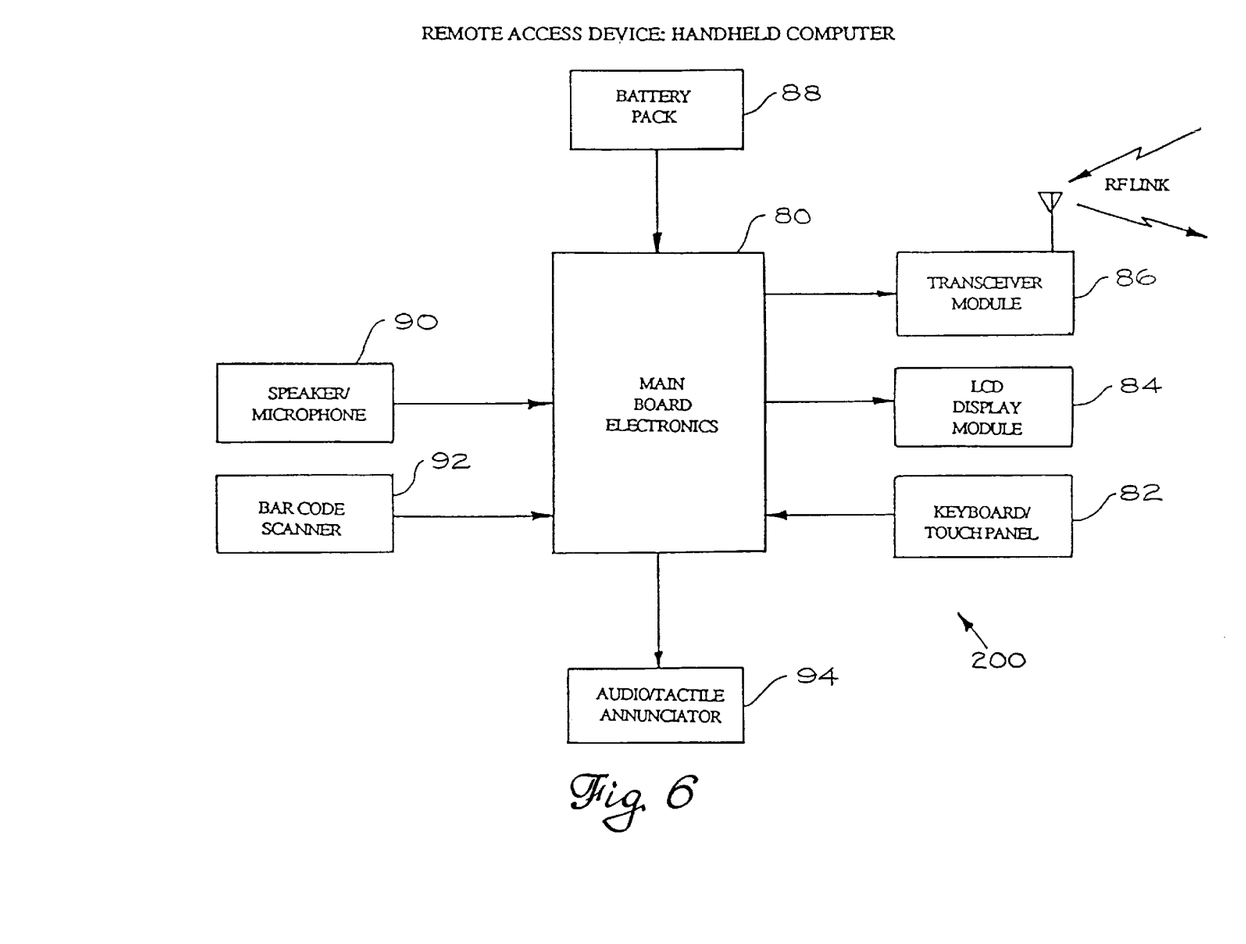
FIG. 6 is a block diagram of one embodiment of a remote access device constructed in accordance with the present invention.
Figure 7:
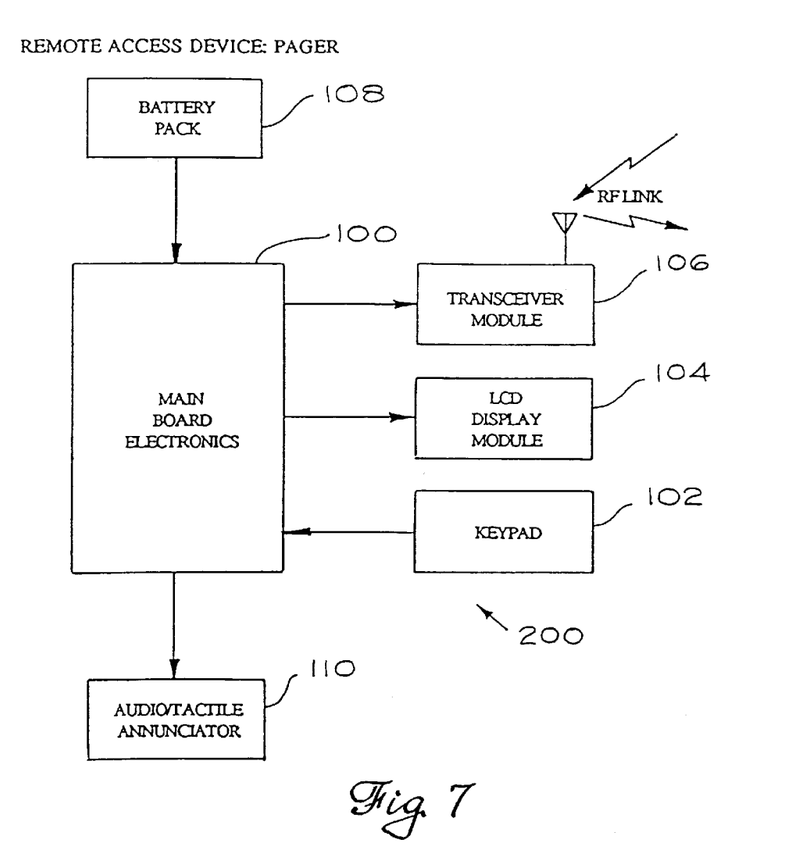
FIG. 7 is a block diagram of an alternative embodiment of a remote access device constructed in accordance with the present invention.

Referring now to FIGS. 6 and 7, two types of remote access devices 200 are shown. FIG. 6 shows a remote access device 200 comprising a hand-held computer or personal digital assistant (PDA). This remote access device preferably comprises a main electronics board 80 comprising a processor and a memory component; a keyboard 82 or other input device, such as a touch panel; a display module 84, which is preferably LCD but may comprise other types of known displays; a transceiver module 86 for communicating over an RF link; a battery pack 88; a microphone and speaker 90; a bar code scanner 92; and an audio/tactile annunciator 94, such as a vibrational device or an audio alarm.

FIG. 7 shows a simpler remote access device 200 similar to a traditional pager. This remote access device preferably comprises a main board 100, including a processor and a memory storage component; a keypad 102 or other input device; a display module 104; a transceiver module 106; a battery pack 108 or other power supply; and an audio/tactile annunciator 110.

Although two types of remote access devices 200 are shown, it will be apparent to one of ordinary skill in the art that any number of such devices with varying features could be constructed. Such devices would require an RF or other transceiver for communicating with the medical monitoring system 10, an alarm signal, a power supply and preferably a display. Other components and features may vary, depending on the expected application. Examples of remote access devices 200 includes pagers, telephones, handheld computers, and personal data assistants (PDAs). Preferably, the remote access device includes one or more of the following: text/graphical display; touch screen; keypad; microphone; speaker; or bar code scanner.

As noted above, the central monitoring systems 14 communicates bi-directionally with at least one, and preferably a plurality of shared, remote access devices 200 carried by caregivers. The remote access devices 200 can request that specific data be transmitted to the access device 200 for review by a caregiver. Alternatively, a central monitoring system 14 can transmit a message, typically indicative of a medical alert, to one or a group of remote access devices 200. The message can contain patient identification and location, alert information, numeric vital signs, and signal waveform data, or arbitrary contents entered through a keyboard or other input device. Because the remote access device preferably operates on the RF spread spectrum communication system, significantly more data can be transferred than in normal paging operations. The message can be initiated manually, in prompted fashion after an alert condition occurs, or automatically after an alert condition occurs. The message may contain static information suitable for a viewing device with limited capabilities such as a pager, or dynamic information (e.g., continuously updated signal waveforms) requiring a more sophisticated viewing device.

The bi-directional communications with remote access device 200 permits the central monitoring system 14 to recognize (a) whether the message successfully reached the target remote access device(s); (b) whether someone actuated the remote access device 200 and opened the message; and (c) whether the caregiver responded with a reply. The same communications technology permits the initiation of a message at the remote access device 200 directed to another such device or the central monitoring system 14, including forwarding of a received message. In this way, nurses or other personnel can be reached with critical information about a patient while performing activities in locations other than a central monitoring system 14. In some applications, free-form tests may be entered at the remote access device 200 and forwarded to another component in the medical monitoring system, usually the central monitoring system 14. This free-form text can be used to provide a password to verify that a message has been received by the intended recipient.

In accordance with yet another preferred embodiment of the invention, the central monitoring system 14 can communicate with auxiliary systems 202 to send and receive patient data for storage, display, analysis, and retrieval. The information transmitted may include patient demographics, clinical data, scheduling information, etc. The auxiliary system 202 may be a diagnostic workstation performing advanced analyses, a clinical information system, or an archival system. Communications may be via hardwired (e.g., serial or network) or wireless communications. Preferably components which require data entry or access will include bar code scanners or other electronic entry devices.

A preferred embodiment of an auxiliary system 202 communicating with the central monitoring system 14 is the diagnostic ECG analysis workstation available under the MicroView trademark from Criticare Systems, Inc. of Waukesha, Wis. The MicroView incorporates arrhythmia, pacemaker, ST and heart rate variability analysis and report generation software. Receiving clinical data for a plurality of patients from a plurality of central monitoring systems, the MicroView analyzes and archives the clinical data. Preferably, large amounts of data can be stored to an optical dish for archival purposes.

A preferred embodiment of a remote access device is the medical alert pager available from Criticare Systems, Inc. of Waukesha, Wis. The pager communicates bi-directionally with the central monitoring system via spread-spectrum RF. It is capable of displaying static text and graphics on a built-in LCD display, typically transmitted from the central monitoring system during an alert situation. An operator can choose a pre-defined response to a message, or compose a text message through a keypad. It will be understood that a variety of portable devices can provide similar or enhanced capabilities, including laptop computers, handheld computers, personal data assistants, and advanced telephones. An additional feature of the medical monitoring system 10 is the ability to transfer large amounts of data concerning a given patient between various components of the system. For example, when a patient is transferred, monitored data concerning this patient may be located in a memory component of the first central monitoring system 14, a memory component of the patient monitor 16 which monitors the patient throughout the transfer and at a second central monitoring system 14 which remotely monitors the patient's new location. To consolidate this information, a transfer function may be selected at any of the first or second central monitoring systems 14 and at the patient monitor 16. Upon receipt of a transfer signal, a patient identity, and a transfer location, patient data can be transferred to the selected network, either through an RF, or a hardwired network. The receiving central monitoring system 14, can then use this information in continuous event monitoring and other monitoring applications. The transfer function may also be used to download relevant patient data from a patients monitor 12 or a central monitoring system 14 to an auxiliary system 202 for analysis or to maintain an overall patient database. Preferably, a bar code coupled to the patient the patient's chart, or other patient data is scanned by the bar code scanner 206 coupled to the central monitoring system 14 or the bar code scanner 204 coupled to the patient monitor 16. The coding of data in this way prevents errors in transmitting data. The ability to transfer monitoring data such as waveforms and vital sign statistics to a clinical information system minimizes the need to maintain patient charts, while the bar-coding system minimizes the risk of manual input errors.

While preferred embodiments of the invention have been shown and described, it will be clear to those skilled in the art that various changes and modifications can be made without departing from the invention in its broader aspects as set forth in the claims provided hereinafter.

What is claimed is:

1. A method for monitoring a plurality of physiological parameters of a patient, comprising the steps of:
providing at least one central monitoring system for monitoring a plurality of physiological parameters, wherein each central monitoring system includes a first transceiver and a memory component;
coupling a patient monitor having a second transceiver and a memory component to said patient to monitor at least one said physiological parameter;
continually transmitting a first data signal corresponding to said physiological parameters from said patient monitor to the central monitoring system;
storing physiological data in the memory component of the central monitoring system;
transmitting a second data signal from the central monitoring system to said patient monitor to remotely select at least one of the plurality of physiological parameters to be monitored;
displaying a continuous representation of at least one physiological parameter on a display coupled to the central monitoring system;
providing a bi-directional communications link between the central monitoring system and at least one remote access device to allow bi-directional communication between the remote access device and the central monitoring system from a location remote from the central monitoring system, the remote access device including a transceiver and a memory component; and selectively transmitting physiological data from the central monitoring system to the remote access device.

2. The method as defined in claim 1, further including the steps of remotely selecting from among a plurality of ECG lead views transmitted by the patient monitor at the central monitoring system, and automatically switching between the plurality of ECG lead views to obtain an optimal view at the central monitoring system.

3. The method as defined in claim 1, further including the step of displaying a representation of physiological parameters versus patient activity.

4. The method as defined in claim 1, further including the steps of providing a second central monitoring system, transferring the patient, automatically switching monitoring control from the first-mentioned central monitoring system to the second central monitoring system as the patient is transferred, and transmitting physiological data related to the patient from a memory storage component of the first central monitoring system to the memory storage component of the second central monitoring system.

5. The method as defined in claim 1, further including the steps of providing a second central monitoring system, transferring the patient, switching monitoring control from the first-mentioned central monitoring system to the patient monitor when the patient is in transit, storing physiological data in the memory component of the patient monitor while the patient is in transit, switching monitoring control to the second central monitoring system when the patient reaches a new stationary location, and transmitting stored physiological data relating to the patient from the first central monitoring system to the second central monitoring system and from the patient monitor to the second monitoring system.

6. The method as defined in claim 1, further including the steps of providing a plurality of remote access devices, selecting at least one primary recipient and at least one secondary recipient from the plurality of remote access devices, transmitting at least one message from the central monitoring system to the primary recipient, waiting for a response from the primary recipient, and transmitting the message from the primary recipient to the secondary recipient when the response from the primary recipient is not received within a preselected time period.

7. The method as defined in claim 6, wherein the transmitted message includes at least one of: a patient identification data item, a patient location data item, a medical alert data item, a textual patient data message, a numerical patient data message, a static signal waveform, a dynamic signal waveform, a time and date stamp, or a free-format text message.

8. The method as defined in claim 6, wherein each response to a transmitted message includes at least one of: a message received signal; a message opened for reading signal; a message forwarded to another remote access device signal; or a reply transmitted signal.

9. The method as defined in claim 1, wherein the central monitoring system transmits clinical data to at least one auxiliary system, and wherein the central monitoring system receives clinical data from the auxiliary system.

10. The method as described in claim 1, further comprising the steps of periodically accessing a memory component of the remote access device, determining a date and a level of importance of data stored in the memory component of the remote access device, and deleting selected data from the memory component of the remote access device.

11. The method as defined in claim 1, further comprising the steps of analyzing physiological data at the central monitor for a medical alert situation and transmitting physiological data when a medical alert situation is found.

12. The method as defined in claim 1, further comprising the steps of transmitting a data request signal from the remote access device to the central monitoring system and transmitting physiological data from the central monitoring system to the remote access device when the data request signal is received.

13. The method as defined in claim 1, wherein the physiological data selectively transmitted from the central monitoring system to the remote access device comprises a dynamic waveform of a physiological parameter.

14. The method as defined in claim 1, further including the steps of providing a plurality of remote access devices, selecting at least one primary recipient and at least one secondary recipient from the plurality of remote access devices, transmitting at least one message from the central monitoring system to the primary recipient, waiting for a response from the primary recipient, and transmitting the message from the primary recipient to the secondary recipient if the primary recipient fails to acknowledge receipt of the message.

15. A medical monitoring system comprising:
at least one patient monitor including a plurality of sensors for collecting information representing the physiological condition of a patient and a transmitter for transmitting at least one signal representing the physiological condition of a patient, the patient monitor further including a receiver and a display;
at least one central monitoring system, said central monitoring system including a transmitter, a receiver, and a display, the central monitoring system remotely controlling at least one physiological monitoring parameter of at least said one patient monitor;
at least one remote access device, other than a patient monitor, providing bi-directional access to the central monitoring system from a location remote from the central monitoring system, said remote access device including a transmitter and a receiver, the remote access device receiving physiological data from the central monitoring system and transmitting a response to the central monitoring system indicating that the data has been received; and
a communications network providing communications between the central monitoring system, the patient monitor, and the remote access device.

16. The medical monitoring system as defined in claim 15, further comprising an auxiliary system which is linked to the central monitoring system, the patient monitor, and the remote access device through the communications network.

17. The medical monitoring system as defined in claim 16, wherein the auxiliary system is a clinical information system.

18. The medical monitoring system as defined in claim 15, wherein the central monitoring system provides a medical alert signal to the remote access device.

19. The medical monitoring system as defined claim 15, wherein the remote access device is selected from the group consisting of a pager, a portable computer, and a personal data assistant.

20. The medical monitoring system as defined in claim 15, wherein the communications network comprises an RF spread spectrum communications link in the ISM band.

21. A method for providing an integrated patient monitor and medical alert system, comprising the steps of:
linking at least one patient monitor, at least one central monitoring system, and at least one remote access device through a communications network;
periodically evaluating a message memory component of the remote access device to determine an amount of free memory;
selectively deleting messages from the memory message component to increase the amount of free memory;
coupling the patient monitor to a patient;
collecting physiological data from the patient;
analyzing the physiological data of the patient for at least one of a plurality of medical alert situations; and
transmitting a medical alert message to the remote access device when the amount of free memory in the remote access device is sufficient to store the message.

22. The method as defined in claim 21, further comprising the steps of reviewing the memory component in the remote access device to determine a time and date when each of a plurality of messages stored in the remote access device was received at the remote access device, determining a priority level for each of the messages stored in the remote access device, and determining which of the plurality of messages to delete.

23. The method as defined in claim 22, further comprising the steps of periodically transmitting a signal to a plurality of remote access devices, waiting for a response from each remote access device to determine whether the respective remote access device is active, and transmitting the medical alert to a secondary remote access device when a primary remote access device is inactive and the secondary remote access device is active.

24. The method as defined in claim 21, further comprising the steps of determining when a message has been received at the remote access device and when a message has been opened at the remote access device.

25. The method as defined in claim 24, further comprising the steps of linking a plurality of other remote access devices to the communications network, assigning a primary recipient for the message to a first one of the remote access devices and at least one secondary recipient for the message to a second one of the remote access devices.

26. The method as defined in claim 21, further comprising the steps of waiting for a response from the remote access device for a predetermined period of time, and forwarding the message to a second remote access device when the predetermined period of time has elapsed.

27. The method as defined in claim 21, wherein the message transmitted to the remote access device comprises at least one of: a patient identification data item, a patient location data item, a medical alert data item, a textual patient data message, a numerical patient data message, a static signal waveform, a dynamic signal waveform, a time and date stamp, or a free-format text message.

28. The method as defined in claim 21 further comprising the steps of periodically transmitting a signal to the remote access device, waiting for a response from the remote access device to determine whether the remote access device is active, and transmitting the medical alert to the remote access device when the remote access device is active.

29. The method as defined in claim 21 wherein the physiological data is analyzed by the patient monitor.

30. The method as defined in claim 21 wherein the physiological data is analyzed by the central monitoring system.

31. A medical monitoring system comprising:
at least one patient monitor, said patient monitor including a transmitter, a receiver, a display, and a plurality of sensors for collecting and transmitting at least one signal representing the physiological condition of a patient;

at least one central monitoring system, said central monitoring system including a transmitter, a receiver, and a display, said central monitoring system remotely controlling at least one physiological monitoring parameter of at least one patient monitor;

at least one remote access device including a transmitter for communicating with the central monitoring system to request specific data for review, and a receiver for receiving the data requested from the central monitoring system; and a communications network providing communications between the central monitoring system, the patient monitor, and the remote access device, wherein at least one of the patient monitor, the central monitoring system, and the remote access device includes an electronic data entry device.

32. The medical monitoring system as defined in claim 31, wherein the electronic data entry device comprises a barcode scanner.

* * * * *